US008753693B2

(12) United States Patent
Archambault et al.

(10) Patent No.: US 8,753,693 B2
(45) Date of Patent: Jun. 17, 2014

(54) COSMETIC COMPOSITION CONTAINING AN EXTRACT FROM LOTUS AND METHOD OF COSMETIC CARE USING SAID COMPOSITION

(75) Inventors: Jean-Christophe Archambault, Meung sur Loire (FR); Jocelyne Franchi, Saint Jean de la Ruelle (FR); Rodolphe Korichi, Saint Jean le Blanc (FR)

(73) Assignee: LVMH Recherche, Saint Jean de Braye (FR)

( * ) Notice: Subject to any disclaimer, the term of this patent is extended or adjusted under 35 U.S.C. 154(b) by 996 days.

(21) Appl. No.: 12/316,144

(22) Filed: Dec. 10, 2008

(65) Prior Publication Data

US 2009/0148544 A1 Jun. 11, 2009

(30) Foreign Application Priority Data

Dec. 10, 2007 (FR) ...................................... 07 08590
Dec. 5, 2008 (FR) ...................................... 08 58318

(51) Int. Cl.
*A61K 36/00* (2006.01)
(52) U.S. Cl.
USPC ......................................................... 424/725
(58) Field of Classification Search
None
See application file for complete search history.

(56) References Cited

U.S. PATENT DOCUMENTS

| 2002/0098253 | A1 | 7/2002 | Riley | |
| 2005/0255077 | A1* | 11/2005 | Golz-Berner et al. | ........... 424/74 |
| 2007/0269415 | A1 | 11/2007 | Goto et al. | |

FOREIGN PATENT DOCUMENTS

| CN | 101 020 007 | A | 8/2007 |
| DE | 10 2005 26357 | A1 | 12/2006 |
| DE | 10 2005 030864 | A1 | 1/2007 |
| FR | 2 834 887 | A1 | 7/2003 |
| JP | 01061415 | A * | 3/1989 |
| JP | 2000-297044 | A | 10/2000 |
| JP | 2004137191 | A * | 5/2004 |
| KR | 2005028272 | A * | 3/2005 |
| KR | 2006 034 007 | A | 4/2006 |
| KR | 2006 065 749 | A | 4/2006 |
| KR | 2007 0070659 | A | 7/2007 |
| KR | 2007 0103173 | A | 10/2007 |

OTHER PUBLICATIONS

Zondlo, Final report on the safety assessment of Tocopherol, Tocopheryl Acetate, Tocopheryl Linoleate, Tocopheryl Linoleate/Oleate, Tocopheryl Nicotinate, Tocopheryl Succinate, Dioleyl Tocopheryl Methylsilanol, Potassium Ascorbyl Tocopheryl Phosphate, and Tocophersolan, International journal of toxicology, (2002) vol. 21 Suppl 3, pp. 51-116.*
Saeed et al, The essential oil of Nymphaea hybrida Tach V. and Nelumbo nucifera Gaertn. Egypt. J. Pharm. Sci., 36 (1-6): 353-359 (1995).*
Takai, N. et al. "Effect of psychological stress on the salivary cortisol and amylase levels in healthy young adults", Archives of Oral Biology, vol. 49, 2004, pp. 963-968.
"Paresse" ADDIACTIVE, online, No. 54, Sep. 2006, XP002531548, pp. 1-23.
"Kenzoki Hyper-active serum", Cosmetics Ingredients Collection, online, Feb. 27, 2007, XP002531547, URL:http://blog/tianya.cn.

* cited by examiner

*Primary Examiner* — Qiuwen Mi
(74) *Attorney, Agent, or Firm* — Hamre, Schumann, Mueller & Larson, P.C.

(57) ABSTRACT

The invention relates to a cosmetic composition containing at least one extract from at least one part of the Sacred Lotus plant (*Nelumbo nucifera*) in a cosmetically acceptable vehicle compatible with topical application on the skin, wherein said composition contains an aqueous extract of Sacred Lotus root and it additionally contains at least one active agent selected from the group comprising active agents with energizing or revitalizing activity, preferably diguanosine polyphosphate or an extract containing it; active agents stimulating the secretion of beta-endorphins, preferably an N-acetyl-Tyr-Arg-hexadecyl ester dipeptide; anti-radical agents such as tocopherol, and plant extracts containing them as well as flavonoids and anthocyanins and plant extracts containing them, in particular extracts of Sacred Lotus flower and anti-inflammatory agents, in particular those having a phospholipase A2 inhibitory action.

17 Claims, No Drawings

COSMETIC COMPOSITION CONTAINING AN EXTRACT FROM LOTUS AND METHOD OF COSMETIC CARE USING SAID COMPOSITION

The invention relates to a cosmetic composition containing an extract from Lotus and a method of cosmetic care using said composition.

The Sacred Lotus (*Nelumbo nucifera* Gaertn.) is an aquatic plant of the family Nelumbonaceae, which occurs notably in south-east Asia.

It is a perennial plant with a stalk in the form of a spongy, thick, branched rhizome, having tubercles fixed in the bottom of the pond, and flowers, of a whitish-pink color, with diameter of 15 to 30 cm and with about twenty petals.

Many cosmetic uses of extracts of Sacred Lotus have already been described.

The present invention relates, however, to a novel cosmetic use of an extract from Sacred Lotus, notably for the care of skin that is under stress.

This novel use is quite particularly suitable for the care of sensitive skin.

In fact, sensitive skin is characterized by a tendency to hyperreactivity relative to normal skin when it is subjected to the same stimulus, and in particular to an environmental stimulus.

This hyperreactivity is manifested by tingling, redness, hotness, formication or itching, sometimes accompanied by redness.

The environmental stimuli that trigger or induce such reactions can be of a physical (UV radiation, temperatures etc.), chemical (pollution etc.), hormonal (menstrual cycle) or emotional nature (stress) (Morizot et al. Cosmetics and toiletries, 2000, 115 (11), p. 83-89).

Some authors have shown that CGRP (calcitonin gene-related peptide), which is the peptide linked to the calcitonin gene, is a neuromediator, which at the level of the neurosensory cells of the skin, is involved in the inflammatory reaction induced for example by irradiation of the skin with ultraviolet (UV) radiation (Scholzen et al., J Investig. Dermatol. Symp. Proc., 1999; 4(1): 55-60).

It has been shown that the neuropeptide CGRP released by the nerve cells of the skin stimulates endothelial cells of the dermis to release interleukin 8 (IL-8), an important mediator of skin inflammation (Ansel et al., J Investig. Dermatol. Symp. Proc., 1997; 2(1):23-26).

Stress-related effects are often expressed at cutaneous level more intensely in people who have sensitive or reactive skin.

Stress is defined here as the tension that results from adaptation of the body when faced with situations that are unusual or are perceived as such.

Stress is therefore a subjective reality that depends both on the nature and character, predictable or not, of the stressful element and on the manner in which the individual perceives and experiences it.

Researchers have shown that the perception of a stress at the level of the central nervous system is transmitted to the peripheral organs such as the skin, by means of neurotrophins and neuropeptides.

CGRP is one of the neuropeptides that is involved in the creation of a state of irritation at cutaneous level, by exacerbating the sensations of discomfort (tugging pain or tingling) that occur more particularly in people who have a sensitive skin.

In particular, it has been demonstrated that in rats subjected to stress, in this case a stress caused by sound, the amount of CGRP released by the sensitive fibers of the skin is significantly increased (Joachim et al., J Mol Med., 2007 Jul. 17).

Furthermore, cortisol is a hormone that is usually designated as the "stress hormone".

Cortisol is a corticosteroid hormone secreted by the adrenal cortex from cholesterol and under the influence of pituitary ACTH.

Some authors have shown that the level of salivary cortisol in the oral cavity undergoes changes during episodes of stress, and that this hormone is released more particularly during negative events that generate stress (Smyth, et al., Psychoneuroendocrinology 1998; 23:353-370).

Thus, salivary cortisol constitutes an interesting marker for revealing the effect of stress.

Another marker is alpha-amylase.

Alpha-amylase is a salivary enzyme that has been shown in recent works to be another marker of stress.

Thus, it has been suggested that the salivary secretion of alpha-amylase in response to stress corresponds to activation of the sympathetic nervous system (Rohleder et al., Ann. N.Y. Acad. Sci., 2004, 1032, 258-263).

Studies have shown a correlation between measurement of the activity of salivary alpha-amylase before, and then just after, a stressful episode and the mental state of the subject undergoing the test (Yamaguchi, Proceedings of the 25th Annual International Conference of the IEEE, 2003, 4, 3075-3078).

A study for the purpose of comparing the variation of these two salivary markers, cortisol and alpha-amylase, in the course of episodes of psychological stress concluded that salivary alpha-amylase increased more significantly and more quickly than salivary cortisol, in response to a psychological stress, suggesting that this enzyme is a better indicator of stress, as well as of relaxation and alleviation (Takai, Arch. Oral Biol., 2004, 49 (12), 963-968).

The applicant verified, firstly, using a model of co-culture of sensory neurons and keratinocytes, that an aqueous extract of Sacred Lotus root displays a favorable effect of inhibition of the secretion of CGRP, a neuromediator involved in skin reactivity, by the sensory neurons.

The applicant then demonstrated that aqueous extracts of Sacred Lotus root, combined with various actives, and optionally with other extracts from the same plant, made it possible to prepare compositions leading to a significant decrease in the effects of stress. This effect was demonstrated by measuring the aforementioned salivary markers.

Such compositions, which constitute novel products, display remarkable properties, making it possible both to limit the negative effects on the skin linked to environmental factors such as stress, and to exert a calming and soothing effect on the skin in the case of exacerbated manifestations of said environmental factors, in particular of stress, on sensitive skin.

Moreover, these compositions, owing to the presence of other active substance(s) and quite particularly of an additional extract from the same plant, display, in addition to a soothing and calming effect on the skin, principally linked to the presence of the aqueous extract of Sacred Lotus root which limits the production of CGRP, various other properties which act in synergy with this effect and lead to compositions which make it possible to protect the skin from the various daily tensions or aggressive factors and improve its sensory receptivity.

In fact, owing to the compositions of the invention, the skin enters a true state of relaxation.

Moreover, the presence of at least one of the particular active agents contained in the composition permits even further improvement of the effect obtained by providing at least one additional effect enabling a more relaxed skin to be obtained by a muscle-relaxant effect and/or better protection against free radicals and/or an improvement in the sensory receptivity of the skin and/or stimulation of cellular metabolism.

The presence of the other actives in the composition of the invention makes it possible to obtain at least one of these effects and thus to act in synergy with the main active of the composition (aqueous extract of Sacred Lotus root) to obtain compositions that are particularly suitable for the care of sensitive skin and to provide the skin with a relaxing, calming and soothing effect when it is subjected to various effects of stress and/or gradually obtain relaxed facial features, skin that is smoother and toned, skin that is soothed and softer to the touch, and a bright, radiant complexion.

Thus, according to a first aspect, the invention relates to a novel cosmetic composition containing at least one extract of at least one part of the Sacred Lotus plant (*Nelumbo nucifera*) in a cosmetically acceptable vehicle compatible with topical application on the skin, wherein said composition contains an aqueous extract of Sacred Lotus root and moreover contains at least one active agent selected from the group consisting of:
    active agents with energizing or revitalizing activity,
    active agents stimulating the secretion of beta-endorphins,
    anti-radical agents and
    anti-inflammatory agents.
    According to preferred variants of this first aspect,
    the active agent with energizing or revitalizing activity is diguanosine polyphosphate or an extract containing it, in particular an extract from *Artemia salina*,
    the active agent stimulating the secretion of the beta-endorphins is N-acetyl-Tyr-Arg-hexadecyl ester dipeptide,
    the antiradical agent is an extract from Sacred Lotus flower and
    the anti-inflammatory agent is selected from those that act on phospholipase A2. It is, preferably, a salt of ascorbyl tocopheryl phosphate, preferably potassium ascorbyl tocopheryl phosphate.

According to a second aspect, the invention relates to a method of cosmetic care using the composition that is the object of the first aspect. This method of cosmetic care is intended to provide skin that is subject to the effects of stress with a relaxing, calming and soothing effect and/or gradually obtain relaxed facial features, skin that is smoother and toned, skin that is soothed and softer to the touch, a bright, radiant complexion and comprises the application, on the part of the skin of the face or of the body in question, of an effective amount to obtain the aforementioned effects of a composition that is the object of the first aspect.

Other advantages and characteristics of the invention will become clearer from the detailed description that follows.

Thus, the compositions of the invention contain, as principal active agent, an aqueous extract of Sacred Lotus root and in addition contain at least one complementary active agent.

The results obtained by the applicant have, as already mentioned, made it possible to demonstrate in a test in vitro (co-culture of keratinocytes and sensory neurons) the soothing and neuro-protective effects due to the presence of the principal extract (aqueous extract of Sacred Lotus root).

Moreover, the applicant was able to establish that when this principal extract was combined with at least one complementary active agent as defined above, it was possible to obtain a global effect in vivo on the decrease in the level of salivary cortisol, resulting in an effect of relaxation, comfort and general relaxation.

These various advantages will become clearer from the description that follows.

The principal extract contained in the composition is an aqueous extract of Sacred Lotus root.

According to a particularly interesting variant of the invention, this extract is prepared by a method of vapor entrainment, using water as solvent.

This method of steam entrainment (also called hydrodistillation in the present application) makes it possible in particular to extract volatile compounds that are present in the plant and are soluble in water, in particular volatile aromatic compounds, for example essential oils.

For the application of this method, preferably the plant material used is fresh, i.e. newly harvested and not dried.

According to this preferred method, the extract is obtained by a method of hydrodistillation using exogenous steam, which entrains the soluble volatile compounds contained in the plant.

According to an alternative application of this same method, the extract can be obtained by a method of hydrodistillation that does not include any exogenous supply of steam.

According to this last-mentioned variant of the method, the water of constitution of the plant is vaporized directly by physical means (waves, pressure, temperatures).

Said extract can be obtained in particular by a method of hydrodistillation by microwaves under pulsed vacuum (VMHD), by which the water of constitution of the plant is vaporized under reduced pressure, at a temperature generally below 80° C.

The water vapor, which comes exclusively from the plant itself, entrains the soluble volatile compounds of the plant.

The water vapor collected, enriched in soluble volatile compounds, is then condensed.

The product from the condensation stage is then filtered, and then advantageously sterilized for easier preservation.

Thus, the aqueous extract used by the compositions of the invention is preferably an aqueous extract of Sacred Lotus root (*Nelumbo nucifera*), in particular an extract obtained by hydrodistillation by microwaves under pulsed vacuum (VMHD) described above.

The preferred extract is obtained from fresh, not dried, roots of Sacred Lotus (*Nelumbo nucifera*).

Preferably, this extract contains essential oils.

An example of such an extract is the extract of Sacred Lotus root marketed by the company GATTEFOSSE under the name Extrait Originel® of Lotus.

As pointed out previously, the cosmetic composition of the invention contains, in addition to the principal active agent, namely the aqueous extract of Sacred Lotus root, advantageously obtained by hydrodistillation, at least one complementary active agent which, combined with this aqueous extract of Sacred Lotus root, leads to a global effect in vivo on the decrease in level of salivary cortisol, to lead to the required effect of relaxation, comfort and general relaxation of the composition of the invention.

As pointed out previously, the compositions of the invention contain at least one of the aforementioned reactive components in combination with the principal active agent. Of course, on the contrary, this does not exclude the presence, in the composition of the invention, of several complementary active agents advantageously selected from the categories of actives mentioned above.

The following points should be noted:
1) as anti-radical agents, it is advantageous to select an agent having broad-spectrum anti-radical activity, for optimal limitation of the formation of hydroxyl radicals and of superoxide radicals.

In these conditions, it has proved particularly advantageous to use as anti-radical agent, in the composition of the present invention, an extract from Lotus flower. In fact, by selecting in particular an extract from Lotus flower particularly rich in flavonoids and anthocyanins, it will be possible to obtain a very broad spectrum of anti-radical activity.

That is why the cosmetic compositions of the invention advantageously contain an extract from Sacred Lotus root and an extract from Sacred Lotus flowers.

The extract from Sacred Lotus flower is advantageously obtained by extraction by means of a polar solvent or a mixture of polar solvents selected from the group consisting of water, C1 to C4 alcohols, in particular ethanol, C2 to C6 glycols, in particular glycerol, butylene glycol and propylene glycol, and mixtures thereof.

Thus, the compositions of the invention advantageously contain an extract from Sacred Lotus flowers (*Nelumbo nucifera*), preferably in a butylene glycol/water mixture, preferably an extract rich in flavonoids and anthocyanins.

Such an extract is marketed for example by the company C.E.P SOLABIA under the name Glycolisat BG of Sacred Lotus (flowers).

2) As active agents with energizing or revitalizing activity, it is preferable to select diguanosine phosphate or more preferably an extract containing it, in particular an extract from *Artemia salina*. Such an extract possesses a revitalizing and energizing effect for the cells, by stimulating the synthesis of ATP, which is the principal source of energy essential for cellular metabolism.

3) As anti-inflammatory agents, it is preferable to select an agent that displays phospholipase A2 inhibitory activity and quite particularly ascorbyl tocopheryl phosphates, in particular potassium ascorbyl tocopheryl phosphate. These diphosphates of vitamin E and of vitamin C act by their soothing activity, inhibiting phospholipase A2, which is the enzyme linked to the inflammatory process.

4) As active agents that stimulate the secretion of beta-endorphins, it is preferable to select a lipopeptide with relaxant properties that lowers the frequency of contraction of muscle fibers and stimulates the production of beta-endorphins by the keratinocytes. This lipopeptide is advantageously N-acetyl-Tyr-Arg-hexadecyl ester dipeptide.

As pointed out previously, compositions containing at least one of the complementary actives mentioned above and preferably at least one of the actives in each of the above categories were tested in vivo on a model with assay of salivary cortisol, thus providing evidence of real relaxation provided by the composition of the invention.

Moreover, the cosmetic compositions of the invention advantageously contain a moisturizing agent, in particular glycerol.

For the reasons stated previously, the cosmetic composition of the invention advantageously contains an extract from Sacred Lotus flower, in particular an extract obtained by extraction by means of a polar solvent.

The cosmetic composition of the invention, optionally comprising an extract from Lotus flower as well as the aqueous extract of root, advantageously contains a total content of dry extract of Sacred Lotus between 0.0001 and 5 wt. %, preferably between 0.001 and 2 wt. %, more preferably between 0.01 and 1 wt. % of dry extract.

This composition advantageously contains a total content of dry extract of Sacred Lotus between 0.0001 and 5 wt. %, preferably between 0.001 and 2 wt. %, more preferably between 0.01 and 1 wt. % of dry extract.

The composition according to the invention thus preferably contains from 0.1% to 99%, preferably from 0.1% to 50% by weight of extract from Sacred Lotus or of mixtures of extracts from Sacred Lotus.

The cosmetic composition advantageously contains an extract from Sacred Lotus roots and an extract from Sacred Lotus flowers. According to an advantageous embodiment, it further contains at least one complementary active agent selected from at least one of the four categories mentioned above.

The extract from Sacred Lotus flower is advantageously obtained by extraction by means of a polar solvent or a mixture of polar solvents selected from the group comprising water, C1 to C4 alcohols, in particular ethanol, C2 to C6 glycols, in particular glycerol, butylene glycol and propylene glycol, and mixtures thereof.

As for the proportions of the various constituents of the cosmetic composition of the invention, it is to be noted that, advantageously, the composition contains from 10 to 50 wt. % of an aqueous extract from Sacred Lotus root and from 0.1 to 10 wt. % of an extract from Sacred Lotus flower.

As for the other complementary active agents, when they are present in the solution, they are contained in the following proportions:

0.5 to 5 wt. % of diguanosine polyphosphate or of an extract containing it, in particular of an extract from *Artemia salina*, 0.1 to 5 wt. % of N-acetyl-Tyr-Arg-hexadecyl ester dipeptide, moreover, the composition can also contain, advantageously, from 1 to 15 wt. % of glycerol.

Thus, the composition of the invention advantageously contains an aqueous extract from Sacred Lotus root and an extract from Sacred Lotus flower.

According to a preferred application of the invention, the composition contains from 0.1 to 50 wt. % of aqueous extracts from roots of *Nelumbo nucifera*, from 0.1% to 10 wt. % of extracts from flowers of *Nelumbo nucifera*, and can advantageously also include from 0.5 to 5 wt. % of diguanosine polyphosphate or of an extract containing it, particularly an extract from *Artemia salina*, from 0.1% to 5 wt. % of N-acetyl-Tyr-Arg-hexadecyl ester dipeptide, marketed under the name Calmosensine®, from 0.01% to 2 wt. % of a salt of ascorbyl tocopheryl phosphate and from 1 to 15 wt. % of glycerol.

The cosmetic composition includes at least one cosmetically acceptable excipient, which can be selected from pigments, nacres, dyes, polymers, surfactants, viscosity improvers, perfumes, electrolytes, pH adjusters, antioxidants, preservatives, and mixtures thereof.

The cosmetic composition according to the invention can for example be a serum, a lotion, an emulsion, a cream, tinted or not, or alternatively a hydrogel, preferably a mask, or it can be in the form of a stick or of a patch.

The compositions according to the invention display a particularly desirable calming and soothing effect, and make it possible in particular to obtain relaxed facial features, skin that is smoother and toned, skin that is soothed and softer to the touch, and a bright, radiant complexion, when said extract or said composition is applied on the skin of the face or of the body.

The present invention also relates to a method of cosmetic care using the compositions previously described in an effective amount to provide skin that is subject to the effects of stress, with a relaxing, calming and soothing effect and gradually obtain relaxed facial features, skin that is smoother and toned, skin that is soothed and softer to the touch, a bright, radiant complexion, when said extract or said composition is applied on the skin of the face or of the body.

The compositions according to the invention are intended for application on all or part of the skin of the body or of the face and in particular on the zones of the skin with exacerbated sensitivity, in particular on the face.

The method of cosmetic care is particularly intended for the care of sensitive or reactive skin.

EXAMPLES

Example 1

Activity of an Extract from Roots of (*Nelumbo nucifera*) on the Release of CGRP (Calcitonin Gene-Related Peptide) in a Model of Co-Culture of Sensory Neurons and Keratinocytes The model selected is a co-culture of rat sensory neurons and human keratinocytes. The model is applied to a commercial extract from Sacred Lotus and more precisely to the Extrait Originel® of Sacred Lotus root (*Nelumbo nucifera*), marketed by the company Gattefosse.

The cultures of sensory neurons obtained from spinal ganglia of rat embryos were chosen because the physiology of these neurons is very similar to that of the human sensory neurons. The effects of this aqueous extract are evaluated by measuring the release of CGRP by the sensory neurons.

CGRP (calcitonin gene-related peptide) is a neuromediator involved in skin reactivity by exacerbating sensations of discomfort such as tugging pains or tingling.

In addition, the number of cellular bodies of neurons was evaluated by staining and labeling.

Equipment and Methods
1. Cells Used

Sensory Neurons

Type: Primo culture of sensory neurons prepared according to the technique described by Hall et al. (J Neurosci. 1997; 17(8):2775-84)

Culture medium: DMEM in powder form (Invitrogen 21331) reconstituted in ultrapure water (Merck) buffered with $NaHCO_3$.

L-Glutamine 2 mM (Invitrogen 25030)

Penicillin 50 IU/ml—Streptomycin 50 µg/ml (Invitrogen 15070)

Supplement N2 (17502)

5 ng/ml Nerve Growth Factor (NGF, Invitrogen 13290)

2.5 ng/ml Neurotrophin 3 (NT-3, Tebu 450-03-b)

Human Keratinocytes

Type: Normal human keratinocytes isolated from restorative surgery, used in the third pass (R3K015).

Medium: K SFM (Invitrogen 17005) without supplement.

2. Culture and Treatment of the Sensory Neurons

The spinal ganglia are taken from 15-day rat embryos.

After enzymatic and mechanical dissociation of the ganglia, the cells in suspension were seeded at a density of 15000 cells per well in a 96-well plate in culture medium.

The cells were put in a stove at 37° C. and 5% $CO_2$, moisture-saturated.

After culture for 3 days, the culture supernatants are removed and replaced with:

medium reconstituted from a culture medium in powder form with addition of 100% of ultrapure water.

medium reconstituted from a culture medium in powder form with addition of 25% of the commercial extract under test and 75% of ultrapure water, medium reconstituted from a culture medium in powder form with addition of 50% of the same extract and 50% of ultrapure water.

All these culture media contain 5 ng/mL of NGF and 2.5 ng/ml of NT3. Half of the culture volume was changed every other day.

3. Co-Culture of Sensory Neurons and Keratinocytes

After incubation for 4 days (7 days of culture of the neurons), 10000 keratinocytes were added per culture well, and the cells were incubated for 4 days at 37° C. and 5% of $CO_2$.

4. Treatment and Assay of CGRP

After 4 days of co-culture (11 days of culture of neurons), the culture supernatants are removed and the cells are incubated in the presence of the commercial extract under test with or without capsaicin at $10^{-6}$ M for 25 minutes in a stove at 37° C. and 5% $CO_2$, moisture-saturated.

Each set of experimental conditions was carried out in quadruplicate.

At the end of these incubations, the supernatants were collected and the content of CGRP was measured in the culture supernatants, by an ELISA assay (Rat CGRP enzyme immuno assay Kit A05482) according to the protocol recommended by the supplier.

5. Analysis of the Number of Cell Bodies

At the end of the last-mentioned incubation (12 days of culture of neurons), the cells are fixed in alcohol-acetic acid solution.

The cell bodies of the neurons are labeled with an antibody directed against the protein "Microtubule Associated Protein" (MAP 2) which is an antibody that reacts with the cell bodies of the neurons.

After incubation for 2 hours, the cells are washed in PBS and the labeling is revealed by fluorescent conjugates (GAR Alexa 568).

In parallel, the nuclei were labeled with a solution from Hoechst.

Imaging (3 images per culture well or 12 photographs per experimental condition at magnification ×20) and analysis of the number of cell bodies were carried out using a high-resolution imaging system, InCell Analyzer™ 1000 (GE Healthcare).

Results

The amount of CGRP released by the neurons is referred to the number of neurons (amount of CGRP/average number of neurons per condition) in each of the conditions tested.

The results are presented in the following table:

TABLE 1

Effect of the extract of Sacred Lotus root on the release of CGRP, relative to the number of cell bodies after 8 days of incubation (12 days of culture, including 5 in co-culture with the keratinocytes).

| Culture conditions | Mean value (SD) |
| --- | --- |
| Control medium 100% ultrapure water | 11.2 (1.0) |
| Extract of roots of *Nelumbo nucifera* diluted 25% in water | 8.6 (0.8) |
| Extract of roots of *Nelumbo nucifera* diluted 50% in water | 8.1 (1.2) |
| $P_{pdt}$ | $S_{(p<0.01)}$ |

After incubation for 7 days, in the baseline conditions in the presence of extract of roots of *Nelumbo nucifera* at 25% and 50%, the amount of CGRP released per neuron is significantly inhibited relative to the medium serving as control.

4. Conclusions

The sensory neurons at rest, in culture medium containing the commercial extract of roots of *Nelumbo nucifera*, release significantly less CGRP than the neurons of the control cultures.

The extract tested inhibits the baseline activity relative to the number of neurons, of sensory neurons, and in both sets of conditions (25% and 50%).

However, the extract does not affect the functioning of the neurons, which still have their physiological capacity of stimulation by capsaicin (pigment extract, exciter of the sensory fibers present in the skin).

These results demonstrate the benefit of using said extract of Sacred Lotus root as calming and soothing agent in cosmetic compositions.

Example 2

Cosmetic Cream for the Care of the Face

The cream, with the formula shown below (percentages by weight), is an oil-in-water emulsion:

| | % |
|---|---|
| Purified water | 32.8 |
| Aqueous extract of roots of *Nelumbo nucifera* (Extrait Originel ® marketed by the company Gattefosse) | 25.0 |
| Calmosensine ® | 3.0 |
| Glycerol of plant origin | 2.0 |
| Extract of *Artemia salina* | 1.0 |
| Extract of flowers of *Nelumbo nucifera* (marketed under the name Glycolisat BG ® by the company SOLABIA) | 0.1 |
| Potassium ascorbyl tocopheryl phosphate (Sepivital ®) | 0.05 |
| Emulsified excipients, perfumes and preservatives | qs 100% |

The oil-in-water emulsion is prepared by the conventional methods well known by a person skilled in the art.

The cream thus prepared is intended to be applied on the face.

Example 3

Activity In Vivo of the Composition in Example 2 on Salivary Secretion of Cortisol The cosmetic effect in vivo of facial application of the composition in Example 2 is measured.

The purpose of the study is to measure the salivary levels of cortisol and of alpha-amylase with a special collecting device, and determination by a spectrophotometric method.

Study Protocol

The subjects must not have taken caffeine, alcohol or nicotine the day before the saliva test and must avoid taking vitamin C on the day of the test.

During the hour preceding the collection of saliva, the subjects must not have cleaned their teeth or eaten anything. Moreover, if the subjects are taking hormones, make sure that a period of 12 hours before taking the sample has been respected.

Firstly the participants are at rest for at least the 10 minutes preceding collection of saliva, in a seated position, in a room with controlled humidity (50%±10%) and temperature (22° C.±2° C.).

A single sample of saliva is collected before the composition according to Example 2 is applied on the face.

For collection of the sample of saliva, the subject chews a dental roll of sterile cotton (Salivette®, Sarstedt) for 2 to 3 minutes.

After collection, the saliva sample is put in a suitable tube and then stored at −20° C. until the analysis.

A saliva sample is collected again 10 minutes after applying the composition according to Example 2 on all of the face.

Determination of Cortisol and Alpha-Amylase in Saliva

Kit for Immunoenzymatic Assay of Cortisol in Saliva (Salimetrics, Reference 1-3012)

The method uses monoclonal antibodies of cortisol. The assay is performed on the saliva sample as well as on a cortisol standard.

The cortisol is put in competition with cortisol bound to a peroxidase.

The fraction of cortisol-peroxidase bound to the antibodies is determined by calorimetric reaction with a tetramethylbenzidine (TMB) substrate.

The optical density is measured at 450 nm.

The amount of cortisol-peroxidase is inversely proportional to the amount of cortisol present.

Kit for Assay of Alpha-Amylase in Saliva (Salimetrics, Reference 1-1902)

The method uses a chromogenic substrate, 2-chloro-p-nitrophenol bound to maltotriose.

The enzymatic action of alpha-amylase releases 2-chloro-p-nitrophenol, determined by spectrophotometry at 405 nm.

The activity of the alpha-amylase present in the sample is directly proportional to the increase in absorbance measured at 405 nm.

Summary of the Results

Cortisol

| | Before application T0 | After application T1 | p** |
|---|---|---|---|
| Total panel N = 21 * | 1.27 | 1.00 | $NSlim_{(p=0.11)}$ |
| Increase in salivary cortisol (µg/ml) (n = 6: 25% of the subjects) | 1.17 | 2.02 | $NSlim_{(p=0.08)}$ |
| Decrease or stability of salivary cortisol (µg/ml) (n = 18: 75% of the subjects) | 1.29 | 0.97 | $S_{(-0.02)}$ |

* Three individuals were withdrawn from the panel because of residues that were judged too high during the statistical analysis.

In 21 subjects, cortisol has a tendency to decrease (p=0.11). 75% of the subjects, i.e. 18/24, show a significant decrease in cortisol.

Alpha-Amylase

| | Before application T0 | After application T1 | p* |
|---|---|---|---|
| Total panel N = 21* | 26.1 | 22.2 | $S_{(-0.05)}$ |

*Three individuals were withdrawn from the panel because of residues that were judged too high during the statistical analysis.

In 21 subjects, the level of salivary alpha-amylase decreases significantly after application of the cosmetic composition according to Example 2.

Conclusion

The saliva levels of cortisol and alpha-amylase decrease after application of the cosmetic composition containing a mixture of roots and flowers of *Nelumbo nucifera*.

This decrease indicates a state of alleviation and relaxation, generally reflected at the level of the skin by an improvement in symptoms linked to states of stress. This effect notably makes it possible to use the compositions of the invention for the care of sensitive skin and for obtaining a calming and soothing effect on the skin of the face.

Example 4

Cosmetic Effects of the Composition in Example 2

1. Evaluation of the Moisturizing Effect after 24 Hours

The moisturizing effect is determined by corneometry (n=10 subjects) for 24 hours following application of the composition according to Example 2, on all of the face.

Moisturizing Action
+51% after 2 hours
+51% after 4 hours
+49% after 6 hours
+37% after 24 hours.

The composition displays a significant moisturizing effect for up to 24 hours after application.

2. Evaluation of the Immediate Smoothing Effect on Wrinkles

The smoothing effect on the wrinkles around the eye was determined by measurement before and 1 hour after application of the composition according to Example 2 (n=15 subjects).

A print is taken, and image analysis by cast shadow is also carried out.

The results obtained are as follows:
number of wrinkles: −12%
Corrected mean depth: −13%
Total length: −20%

The smoothing effect of the composition on the wrinkles around the eye is significant.

3. Evaluation of the Anti-Radical Effect

The composition is applied 4 times at intervals of two hours for each application.

The anti-radical activity is evaluated by an ex-vivo method (measurement of D-squame stripping) by determining the level of peroxides by fluorometry.

The measurement is carried out 24 hours after the first application of the test composition, comparing the result with that obtained for an untreated control zone.

We observe a significant decrease, of 28%, in oxygenated reactive species present on the surface of the skin.

What is claimed:

1. A cosmetic composition containing at least one extract of at least one part of the Sacred Lotus plant (*Nelumbo nucifera*) in a cosmetically acceptable vehicle compatible with topical application on the skin, wherein said composition contains:
   (1) an aqueous extract of Sacred Lotus root;
   (2) an extract from Sacred Lotus flower; and
   (3) N-acetyl-Tyr-Arg-hexadecyl ester peptide,
   wherein said composition contains at least one active agent selected from the group consisting of: diguanosine polyphosphate, an extract containing diguanosine polyphosphate, and potassium ascorbyl tocopheryl phosphate.

2. The cosmetic composition as claimed in claim 1, wherein said aqueous extract of Sacred Lotus root is an extract obtained by a method of hydrodistillation.

3. The cosmetic composition as claimed in claim 2, wherein said method of hydrodistillation is a method of hydrodistillation by microwaves under pulsed vacuum (VMHD).

4. The cosmetic composition as claimed in claim 1, further comprising a skin moisturizer.

5. The cosmetic composition as claimed in claim 1, wherein the extract containing diguanosine phosphate is an extract from *Artemia salina*.

6. A cosmetic composition containing an aqueous extract of Sacred Lotus root (*Nelumbo nucifera*), an extract from Sacred Lotus flower (*Nelumbo nucifera*), N-acetyl-Tyr-Arg-hexadecyl ester peptide, an extract from *Artemia salina*, glycerol, potassium ascorbyl tocopheryl phosphate and a cosmetically acceptable vehicle compatible with topical application on the skin.

7. The cosmetic composition as claimed in claim 6, wherein said extract of Sacred Lotus flower is obtained by extraction by means of a polar solvent or a mixture of polar solvents selected from the group consisting of water, C1 to C4 alcohols, C2 to C6 glycols and mixtures thereof.

8. The composition as claimed in claim 1, which contains a total content of dry extract of the Sacred Lotus plant between 0.0001 and 5 wt. %.

9. The cosmetic composition as claimed in claim 1, which contains a total content of extract of the Sacred Lotus plant between 0.1 and 99 wt. % based on the total weight of the composition, of said extract or mixture of extracts.

10. The cosmetic composition as claimed in claim 1, which contains from 10 to 50 wt. % of an aqueous extract from the Sacred Lotus root and from 0.1 to 10 wt. % of an extract from the Sacred Lotus flower.

11. The cosmetic composition as claimed in claim 1, which contains from 0.5 to 5 wt. % of diguanosine polyphosphate or an extract containing it.

12. The composition as claimed in claim 1, which contains 0.1 to 5 wt. % of N-acetyl-Tyr-Arg-hexadecyl ester dipeptide.

13. The cosmetic composition as claimed in claim 1, which contains from 0.01 to 2 wt. % of a salt of ascorbyl tocopheryl phosphate.

14. The composition as claimed in claim 1, which contains from 1 to 15 wt. % of glycerol.

15. The cosmetic composition as claimed in claim 1, which contains from 0.1 to 50 wt. % of aqueous extract of *Nelumbo nucifera* root, from 0.1% to 10 wt. % of extract of flowers of *Nelumbo nucifera*, and from 0.5 to 5 wt. % of diguanosine polyphosphate or an extract containing it, from 0.1% to 5 wt. % of an N-acetyl-Tyr-Arg-hexadecyl ester dipeptide, from 0.01% to 2 wt. % of a salt of ascorbyl tocopheryl phosphate, and from 1 to 15 wt. % of glycerol.

16. A method of cosmetic care, comprising: applying, to the skin of a subject, an effective amount of the composition in accordance with claim 1.

17. The method of cosmetic care as claimed in claim 16, which is intended for the care of sensitive or reactive skin.

* * * * *